United States Patent [19]
Mather et al.

[11] Patent Number: 5,925,679
[45] Date of Patent: Jul. 20, 1999

[54] TOPICAL VEHICLES CONTAINING SOLUBILIZED AND STABILIZED AZELAIC ACID

[75] Inventors: Kamran Mather, Agoura Hills; Christopher Ryan Stahl, Hawthorne, both of Calif.

[73] Assignee: Neutrogena Corporation, Los Angeles, Calif.

[21] Appl. No.: 08/928,704

[22] Filed: Sep. 12, 1997

Related U.S. Application Data

[63] Continuation of application No. 08/469,474, Jun. 6, 1995, abandoned.

[51] Int. Cl.$^6$ .................................................... A61K 31/19
[52] U.S. Cl. .......................... 514/574; 514/859; 514/320
[58] Field of Search .................................. 514/320, 859, 514/574

[56] References Cited

U.S. PATENT DOCUMENTS

| | | | |
|---|---|---|---|
| 4,292,326 | 9/1981 | Nazzaro-Porro | 424/317 |
| 4,386,104 | 5/1983 | Nazzaro-Porro | 424/317 |
| 4,713,394 | 12/1987 | Thornfeldt | 514/574 |
| 4,885,282 | 12/1989 | Thornfeldt | 514/53 |
| 5,549,888 | 8/1996 | Venkateswaran | 424/78.02 |

*Primary Examiner*—Jose' G. Dees
*Assistant Examiner*—Michael A. Williamson
*Attorney, Agent, or Firm*—Richard R. Mybeck

[57] ABSTRACT

A completely solubilized alcohol-free topical composition of azelaic acid in a glycol base which is stable at normal temperatures and which is useful as a commercial substitute for dispersed azelaic acid preparations. The composition has a pH of 4.0 or greater thereby substantially reducing irritation.

9 Claims, No Drawings

TOPICAL VEHICLES CONTAINING SOLUBILIZED AND STABILIZED AZELAIC ACID

The present invention relates to topical compositions containing azelaic acid and glycol and more particularly to new and improved compositions containing stabilized and completely solubilized azelaic acid. This Application is a continuation of U.S. patent application Ser. No. 08/469,474, filed Jun. 6, 1995, now abandoned.

BACKGROUND OF THE INVENTION

This invention relates to a completely solubilized topical formulation of azelaic acid which is stable at normal temperatures. Topical azelaic acid formulations have been used to a wide range of physiological maladies including acne, hyperpigmentary dermatoses, hair loss, wrinkling, hyperhidrosis, non-acne inflammatory dermatoses, infectious cutaneous and ichthyosis.

However, the only topical formulations of azelaic acid presently known are dispersions. Dispersions deliver azelaic acid in an undissolved state. When applied to the skin, undissolved azelaic acid is not readily absorbed and as a result an excess of azelaic acid must be present to be effective. The higher the concentration of azelaic acid, the more likely irritation (burning, stinging and redness) to the skin will occur.

What is needed is a completely solubilized topical azelaic acid composition. Solubilized azelaic acid is much less likely to irritate the skin because azelaic acid in a dissolved state is much more readily absorbed by the skin than in the undissolved states found in dispersions. Better absorption means less azelaic acid need be present in the formulation to be effective thereby lowering the risk of irritation to the skin.

While azelaic acid is somewhat soluble in water, cosmetic oils and alcohols, each of these solvents has serious limitations. Thus, water only marginally dissolves azelaic acid so that a water and azelaic acid solution would contain a maximum of about 0.24% by weight (w/w) azelaic acid, not likely enough to be effective. Azelaic acid has little or no solubility in cosmetic oils. Alcohols are good solvents but are unsatisfactory because large amounts of alcohol e.g., isopropyl alcohol, in a topical composition has the undesirable side effect of drying the skin. Indeed, some alcohols e.g., ethyl alcohol, render azelaic acid unstable at normal temperatures resulting in a totally ineffective composition.

U.S. Pat. Nos. 4,292,326 (Nazzaro-Porro, Sep. 29, 1981), 4,386,104 (Nazzaro-Porro, May 31, 1983), and 4,818,768 (Nazzaro-Porro, Apr. 4, 1989) describe azelaic acid as well as other dicarboxylic acids in the treatment of acne and melanocyclic hyperpigmentary dermatoses. The azelaic acid is dispersed in a cream base.

U.S. Pat. Nos. 4,713,394 (1Thornfeldt, Dec. 15, 1987) and 4,885,282 (Thornfeldt, Dec. 5, 1989) describe of azelaic acid as well as other dicarboxylic acids used in the treatment of nonacne inflammatory dermatoses and infectious cutaneous diseases such as rosacea, perioral dermatitis, eczema, seborrheic dermatitis, psoriasis, tinea cruris, flat warts, and alopecia areata. One of Thornfeldt's formulations comprises azelaic acid disposed in a large proportion of ethanol. While ethyl alcohol dissolves azelaic acid, it also renders the azelaic acid unstable at normal temperatures meaning that it will not provide a marketable product. Thornfeldt's second formulation comprises a complete dispersion of azelaic acid.

An emulsion containing 10–20% concentration of azelaic acid in a base of water, apple pectin and sunflower oil was taught by Berova, N., et al. in "Hypoallergic Cosmetic Emulsion with Azelaic Acid for Prophylaxy and Treatment of Acne Vulgaris," Berova, N., Nkiolova, A., Kratchanov, Chr., and Popova, M., *Journal of Applied Cosmetology*, vol. 12, no. 3, p. 51 (1994). Berova et al. attribute the mildness of their formulation to the use of natural ingredients like apple pectin and sunflower oil instead of non-natural substances in the azelaic acid vehicle. The emulsion taught by Berova et al. is not completely solubilized and suffers from the same problem as do the Nazzaro-Porro and Thornfeldt formulations, the weight percent of azelaic acid in the formulation is higher than needed because the azelaic acid is not completely solubilized.

Venkateswaran U.S. Pat. No. 5,549,888 teaches a solution of active ingredients which includes azelaic acid and is partially solubilized by a glycol. It uses glycol in combination with ethyl alcohol to solubilize the azelaic acid. As stated previously, the presence of ethyl alcohol with azelaic acid can destabilize the azelaic acid. Moreover, because the composition contains ethyl alcohol, formulation of a non-drying, aesthetically pleasing formulation would be difficult. Venkateswaran also teaches that the formulation has a pH between 2.5 and 4.0. This low pH range can have an irritating effect on the skin.

The art has yet to find a formulation for completely solubilizing azelaic acid at normal temperatures without sacrificing the stability of the solubilized azelaic acid. Solubilized azelaic acid must remain stable at normal temperatures in order to provide a marketable product.

Without a stable, completely solubilized formula of azelaic acid, the benefits of azelaic acid are unavailable to many users who experience the burning, stinging and redness of the skin associated with exposure to high levels of undissolved dispersed azelaic acid having an inherent low pH. The present invention provides a completely solubilized and stable formulation of azelaic acid in a glycol base at normal temperatures exhibiting a tolerable pH of 4 or greater and having a shelf life which enables a marketable product to be produced and reduces the amount of azelaic acid the user must be exposed to in order to enjoy its benefits.

BRIEF SUMMARY OF THE INVENTION

The present invention relates to topical compositions of azelaic acid and more specifically to compositions containing stabilized and completely solubilized azelaic acid and glycol which can be used to treat a wide variety of skin conditions. The present invention delivers azelaic acid to the skin in a completely solubilized yet stable form at a tolerable pH, thus insuring excellent absorption by the skin and significantly reducing the incidence of skin irritation.

Accordingly, a primary object of the invention is to provide a stable and completely solubilized formulation containing azelaic acid.

Another object is to provide lower, yet effective, concentrations of a topical azelaic acid formulation that is less likely to irritate the skin of the user.

A further object of the invention is to provide a stable, solubilized azelaic acid formulation that can be stored for long periods at normal temperatures and atmospheric pressures.

A still further object is to provide a completely solubilized and stabilized topical formulation containing azelaic acid that addresses a large variety of skin conditions.

These and still further objects as shall hereinafter appear are fulfilled by the present invention in a remarkably unexpected fashion as will be readily discerned from a careful consideration of the following detailed description of preferred embodiments thereof especially when read in conjunction with the several examples appended thereto.

DESCRIPTION OF THE PREFERRED EMBODIMENT

The present invention relates to a topical cosmetic preparation containing azelaic acid stabilized and completely solubilized in a glycol base. The preparation is used to treat a wide variety of skin ailments with little or no irritation to the skin. The glycol easily and completely dissolves the azelaic acid without affecting the stability of the azelaic acid. The absence of ethanol or other destabilizing solvents insures the azelaic acid remains stable.

Azelaic acid, a straight chain dicarboxylic acid with 9 carbons, has limited solubility in water and commonly used cosmetic oils. However, lower levels of azelaic acid (from about 0.5% (w/w) to about 10% (w/w)) may be completely dissolved in glycol (from about 20% (w/w) to about 60% (w/w)) and remain in stable solution. The glycol utilized may be one or more of the following: propylene glycol, polypropylene glycol, dipropylene glycol, butylene glycol, polyethylene glycol, polyethylene glycol ethers, ethoxydiglycol, and the like. Moreover, if the azelaic acid is completely in solution, less azelaic acid is required for the treatment of the previously mentioned conditions. And unlike ethyl alcohol, the glycols maintain a stable solution at normal temperatures. Glycols also provide humectancy to the formulation, whereas ethyl alcohol or isopropanol have a drying effect.

Of course, other glycols which readily dissolve azelaic acid may be selected. The amount of glycol may vary from about 20% to 60% (w/w). 20% (w/w) glycol is the minimum amount required to solubilize an effective amount of azelaic acid. 60% (w/w) is probably the maximum level that could be used without completely sacrificing the formulation's aesthetics. Somewhere in the middle of this range is most ideal.

Although glycols are effective solubilizers for azelaic acid, the addition of water in a formulation can decrease the solubility of the azelaic acid. When preparing a formulation, a careful ratio between the water and glycols is employed to maintain the azelaic acid in solution even at refrigerated temperatures. The following Table 1 lists the various glycols and the maximum amount of water that can be used in the 1% azelaic acid formulations. The remaining balance of the formula may be other cosmetic ingredients that may include but are not limited to humectants (ie glycerin), emulsifiers, thickeners, opacifying agents, glycol/water compatible emollients. The other ingredients may be used if they do not negatively affect the solubility of the azelaic acid.

TABLE 1

| Solvent (GLYCOL) | % Azelaic Acid | % Glycol | % Water | % Other Ingredients |
| --- | --- | --- | --- | --- |
| Propylene Glycol | 1.10 | 45 | 40 | 13.90 |
| Dipropylene Glycol | 1.10 | 30 | 45 | 23.90 |
| Polypropylene Glycol-9 | 1.10 | 25 | 45 | 28.90 |
| Butylene Glycol | 1.10 | 35 | 45 | 18.90 |
| Polyethylene Glycol-8 | 1.10 | 35 | 40 | 23.90 |
| Polyethylene Glycol-32 | 1.10 | 30 | 40 | 28.90 |
| PEG-6 Methyl Ether | 1.10 | 30 | 45 | 23.90 |
| Ethoxydiglycol | 1.10 | 25 | 50 | 23.90 |
| Hexylene Glycol | 1.10 | 20 | 45 | 33.90 |
| PPG-2 Methyl Ether | 1.10 | 30 | 45 | 27.90 |

To further aid in the understanding of the present invention, and not by way of limitation, the following examples are presented:

EXAMPLE 1

In one practice of the present invention, and our preferred embodiment thereof, a topical cream is produced by mixing about 20.0 to 60.0% (w/w) of ethoxydiglycol, about 3% (w/w) of diisopropyl adipate and about 1.0% to 10.0% (w/w) of azelaic acid until a clear solution is formed. In a separate container, q.s. distilled water and about 5.0% (w/w) of PEG-60 almond glycerides are mixed and heated to 70° C. To this mixture, about 8% (w/w) of glycol distearate is added and all three ingredients are mixed while maintaining a temperature of 70° C. until the whole forms a white homogeneous fluid. This mixture was allowed to cool to 40° C. to which the azelaic acid-ethoxydiglycol-diisopropyl adipate mixture is added. About 2.5% (w/w) of a mixture of polyacrylamide, C13–C14 isoparaffin and Laureth 7, (which mixture is available as SEPIGEL 305 from Seppic Department Cosmetique-Pharacie, Paris, France), is then added and the whole was mixed until a thick and homogeneous cream resulted.

A translucent gel can be made from the above formulation by removing the glycol distearate therefrom.

EXAMPLE 2

In another preferred practice of the present invention, a topical cream is produced by mixing about 1.0% to 10.0% (w/w) of azelaic acid with about 20.0% to 60.0% (w/w) of dipropylene glycol and heating the mixture to about 60° C. until a clear solution is formed. The solution is then cooled to and maintained at 40° C. In a separate container, about 5.0% (w/w) PEG-60 almond glycerides and q.s. distilled water are mixed and heated to about 70° C. To this mixture, about 8.0% (w/w) of glycol distearate is added and all three ingredients are mixed while maintaining a temperature of 70° C. until the whole forms a white homogeneous fluid. This mixture is then allowed to cool to 40° C. and the azelaic acid-dipropylene glycol mixture is added thereto and mixed therein. About 2.0% (w/w) of a mixture of polyacrylamide, C13–C14 isoparaffin and Laureth 7 (SEPIGEL 305) is then added and the whole mixed until a thick and homogeneous cream results.

A translucent gel can be made from the above formulation by removing the glycol distearate therefrom.

Each of the products produced by the foregoing Examples, hereinafter designated "Formula 1" and "Formula 2", respectively (each Formula number corresponding to the Example by which it was produced, was then tested following the methods outlined in: Grove, G. L., Soschin, A. M. and Kligman, A. M., "Guidelines for Performing Facial Stinging Tests," available from Skin Study Center, Simon Greenburg Foundation, 3901 Market Street, Philadelphia, Pa. and the Duhring Laboratories, Department of Dermatology, University of Pennsylvania School of Medicine, Philadelphia, Pa. 19104, and incorporated herein by this reference thereto.

The effectiveness of Formula 1 was tested on a panel of 17 individuals having reddish or hyperpigmented skin. The discoloration of the skin was measured using a MINOLTA CHROMAMETER Model CR-200. The panelists applied Formula 1 to the discolored skin once per day for 4 weeks. At the end of the 4 week period the skin discoloration was again measured using the MINOLTA CHROMAMETER. Results showed a significant reduction of skin discoloration for the group as an average.

The mildness of Formula 2 was tested on a panel of 18 people, some of whom were classified as "stingers." A "stinger" is a person who experiences stinging, burning or itching after an application of 5% lactic acid solution to the naso-labial area of the face. These "stingers" are considered to have sensitive skin. Results of the tests showed that both formulas were considered to be mild using Kligman's scale.

Additional specific formulations were prepared using the general procedures described above to provide the following formulations.

FORMULA 3

| Material | % by weight |
| --- | --- |
| Ethoxydiglycol | 41.5 |
| Azelaic Acid | 1.1 |
| Diisopropyl Adipate | 3.0 |
| PEG-60 Almond Glycerides | 5.0 |
| Glycol Distearate | 8.0 |
| SEPIGEL 305 | 2.5 |
| Distilled Water | to 100% |

Other glycols, such as dipropylene glycol, can be similarly used to solubilize the azelaic acid as in the following Formula 4.

FORMULA 4

| Material | % by weight |
| --- | --- |
| Dipropylene Glycol | 43.75 |
| Azelaic Acid | 1.10 |
| PEG-60 Almond Glycerides | 5.00 |
| Glycol Distearate | 8.00 |
| SEPIGEL 305 | 2.00 |
| Distilled Water | to 100% |

Combinations of glycols can also be used as shown in Formula 5.

FORMULA 5

| Material | % by weight |
| --- | --- |
| Butylene Glycol | 27.5 |
| PEG-32 | 20.0 |
| Azelaic Acid | 1.1 |
| Polysorbate 20 | 4.0 |
| Glycol Distearate | 7.5 |
| Glycerin | 5.0 |
| SEPIGEL 305 | 1.5 |
| Distilled Water | to 100% |

In each of these formulations, an emulsifier (e.g. PEG-60, Almond Glycerides, Polysorbate 20) is employed.

These ingredients serve dual functions: first is to assist in dispersion of other ingredients like the glycol distearate and second is to enhance penetration of the azelaic acid. The emulsifier needs to have a hydrophilic/lipophilic balance (HLB)>13 for these purposes in the amount of 2–10%.

The pH of the formulations all range from 4.0 to 5.0. Typical pH values from the preceding formulas are as follows:

FORMULA 3 pH—4.4
FORMULA 4 pH—4.3
FORMULA 5 pH—4.7

A pH value between pH 4.0 and 5.0 is better tolerated by the skin than formulations having pH values below 4.0 which are to be avoided.

From the foregoing, it is apparent that novel and unique topical vehicles containing solubilized and stabilized azelaic acid have been herein described and illustrated which fulfills all of the aforestated objectives in a remarkably unexpected fashion. It is, of course understood that such modifications, variations or adaptations as may readily occur to an artisan familiar with the art to which this invention pertains are intended within the spirit of this invention which is limited only by the scope of the claims appended hereto.

Accordingly what is claimed is:

1. A topical composition comprising completely solubilized azelaic acid in a glycol base wherein said solubilized azelaic acid is stable at normal temperatures and exhibits a pH of 4.0 or greater; said composition containing from about 0.5% to about 10% (w/w) of said azelaic acid, from about 20.0% to about 60.0% (w/w) of a glycol base, and from about 20.0% to about 60.0% (w/w) distilled water said glycol base being selected from the group consisting of propylene glycol, polypropylene glycol, dipropylene glycol, butylene glycol, polyethylene glycol, polyethylene glycol ethers, polyproprylene glycol ethers, hexylene glycol, and ethoxydiglycol.

2. A topical composition comprising completely solubilized azelaic acid in a glycol base wherein said solubilized azelaic acid is stable at normal temperatures and exhibits a pH of 4.0 or greater; said composition containing from about 0.5% to about 10% (w/w) of said azelaic acid, from about 20.0% to about 60% (w/w) of a glycol base, and from about 20.0% to about 60.0% (w/w) distilled water; said composition further comprising about 20% to about 60% ethoxydiglycol, about 3.0% (w/w) of diisopropyl adipate, about 5.0% (w/w) of PEG-60 almond glycerides, about 8.0% (w/w) of glycol distearate, about 2.5% (w/w) of a mixture of polyacrylamide, C13–C14 isoparaffin and Laureth 7 and q.s. distilled water.

3. The composition according to claim 2 comprising from about 1% to about 10% (w/w) of said azelaic acid.

4. The composition according to claim 3 comprising from at least about 35% up to about 60% (w/w) of glycol base.

5. A topical composition according to claim 2 containing from about 20% up to about 35% (w/w) of a glycol base.

6. A topical composition comprising completely solubilized azelaic acid in a glycol base wherein said solubilized azelaic acid is stable at normal temperatures and exhibits a pH of 4.0 or greater; said composition containing from about 0.5% to about 10% (w/w) of said azelaic acid, from about 20.0% to about 60.0% (w/w) of a glycol base, and from about 20.0% to about 60.0% (w/w) distilled water, said composition further comprising about 20% to about 60% (w/w) dipropylene glycol, about 5.0% (w/w) of PEG-60 almond glycerides, about 8.0% (w/w) of glycol distearate, about 2.0% (w/w) of a mixture of polyacrylamide, C13–C14 isoparaffin and Laureth 7 and q.s. distilled water.

7. The composition according to claim 6 comprising from about 1% to about 10% (w/w) of said azelaic acid.

8. The composition according to claim 7 comprising from at least about 35.0% to about 60.0% (w/w) of glycol base.

9. A topical composition according to claim 6 containing from about 30% up to about 50% (w/w) of a glycol base.

* * * * *